(12) United States Patent
Yamauchi (10) Patent No.: US 10,481,078 B2
(45) Date of Patent: Nov. 19, 2019

(54) HYGROMETER AND TEMPERATURE-HUMIDITY CHAMBER PROVIDED WITH SAME

(71) Applicant: ESPEC CORP., Osaka-shi, Osaka (JP)

(72) Inventor: Satoru Yamauchi, Sanda (JP)

(73) Assignee: ESPEC CORP. (JP)

( * ) Notice: Subject to any disclaimer, the term of this patent is extended or adjusted under 35 U.S.C. 154(b) by 114 days.

(21) Appl. No.: 14/391,025

(22) PCT Filed: Mar. 6, 2013

(86) PCT No.: PCT/JP2013/001392
§ 371 (c)(1),
(2) Date: Oct. 7, 2014

(87) PCT Pub. No.: WO2013/157185
PCT Pub. Date: Oct. 24, 2013

(65) Prior Publication Data
US 2015/0068283 A1    Mar. 12, 2015

(30) Foreign Application Priority Data
Apr. 16, 2012    (JP) .................. 2012-093367

(51) Int. Cl.
*G01N 19/10*    (2006.01)
*G01N 25/66*    (2006.01)

(52) U.S. Cl.
CPC ............ *G01N 19/10* (2013.01); *G01N 25/66* (2013.01)

(58) Field of Classification Search
None
See application file for complete search history.

(56) References Cited

U.S. PATENT DOCUMENTS 4,826,327 A    5/1989   Michell
5,148,710 A    9/1992   Gudehus
(Continued)

FOREIGN PATENT DOCUMENTS

CN    2039423 U    6/1989
CN    1512163 A    7/2004
(Continued)

OTHER PUBLICATIONS

"Kitchen Design Ideas for Your New Home"; Date: Mar. 13, 2011: pp. 1-9.*
(Continued)

*Primary Examiner* — Judy Nguyen
*Assistant Examiner* — Ruben C Parco, Jr.
(74) *Attorney, Agent, or Firm* — Gerald E. Hespos; Michael J. Porco; Matthew T. Hespos (57) ABSTRACT

A hygrometer includes a heat transfer section extending from a measurement space toward an outside space separated from the measurement space, a heat release amount control unit that causes heat to be released to the outside space from the heat transfer section such that an amount of heat released to the outside space is made constant, and a computation device that calculates a humidity of the measurement space. The computation device calculates the humidity from a heat transfer section temperature and a measurement space temperature using a relational expression based on a heat balance in the heat transfer section when condensation is occurring in a portion, of the heat transfer section, located within the measurement space in a state where the amount of heat released to the outside space from the heat transfer section is made constant by the heat release amount control unit.

5 Claims, 8 Drawing Sheets

(56) References Cited

U.S. PATENT DOCUMENTS

| | | | | | |
|---|---|---|---|---|---|
| 5,165,793 | A | * | 11/1992 | Rall | G01N 25/68 374/16 |
| 5,272,963 | A | * | 12/1993 | Del Fabbro | A21B 3/04 126/20 |
| 6,712,504 | B1 | * | 3/2004 | Dai | G01N 25/56 374/141 |
| 8,090,477 | B1 | * | 1/2012 | Steinberg | G05D 23/1923 700/276 |
| 2003/0036052 | A1 | * | 2/2003 | Delwiche | C12Q 1/001 435/4 |
| 2004/0138830 | A1 | | 7/2004 | Yamamoto | |
| 2005/0034716 | A1 | * | 2/2005 | Harbin | A47J 37/01 126/25 R |
| 2006/0234621 | A1 | * | 10/2006 | Desrochers | F24F 3/044 454/239 |
| 2010/0040106 | A1 | | 2/2010 | Sakami | |
| 2012/0287961 | A1 | | 11/2012 | Sakami | |

FOREIGN PATENT DOCUMENTS

| | | |
|---|---|---|
| CN | 1632546 A | 6/2005 |
| CN | 1645117 A | 7/2005 |
| DE | 4005744 C1 | 11/1991 |
| JP | 61-75235 | 4/1986 |
| JP | 4837777 | 12/2011 |
| JP | 2012-83206 | 4/2012 |
| WO | 2008/123313 | 10/2008 |
| WO | WO-2011110197 A1 * | 9/2011 ............. G01N 25/68 |

OTHER PUBLICATIONS

Title: May 19, 2016 Memo; URL: https://www.uspto.gov/sites/default/files/documents/ieg-may-2016_enfish_memo.pdf; date: May 2016.*
Title: Nov. 2, 2016 Memo; URL: https://www.uspto.gov/sites/default/files/documents/McRo-Bascom-Memo.pdf; date: Nov. 2016.*
Satoru Yamaguchi et al., "Shitsujun Kuki no Gyoshuku o Mochiita Dennetsushiki Shitsudokei no Kaihatsu", National Heat Transfer Symposium of Japan Koen Ronbunshu (CD-ROM), 2011. 06, 48th, Ronbun No. G212.
"Development of Heat Transfer Hygrometer using Moisture Condensation" by ESPEC Corp., et al., from Lecture-proceeding Documents for the 59th Union Forum concerning Applied Physics at Waseda University in Spring, 2012.
International Search Report dated May 22, 2013.
Taiwanese Office Action dated Dec. 14, 2015.
Chinese Office Action dated Feb. 28, 2018.

* cited by examiner

HYGROMETER AND TEMPERATURE-HUMIDITY CHAMBER PROVIDED WITH SAME

TECHNICAL FIELD

The present invention relates to a hygrometer and a temperature-humidity chamber provided with the hygrometer.

BACKGROUND ART

As disclosed in Japanese Patent No. 4837777, a hygrometer is known in which the humidity within a measurement space can be measured using a heat transfer section such as, for example, a heat pipe arranged across the measurement space and an outside space partitioned from each other by a thermal insulation section.

As an improvement of the hygrometer, the applicant of the present application has proposed a hygrometer below (see Japanese Patent Laid-open No. 2012-083206).

Specifically, with the hygrometer disclosed in Japanese Patent Application Laid-open No. 2012-083206, the humidity of a measurement space is obtained by computation from the temperature of a heat transfer section, the temperature of the measurement space, and the temperature of an outside space that are detected in a state where dew formation has been generated in a portion, of the heat transfer section, located within the measurement space.

In the hygrometer disclosed in Japanese Patent Application Laid-open No. 2012-083206, the temperature of the outside space is used in computation upon obtaining the humidity of the measurement space. Therefore, even if the humidity of the measurement space is constant, there are cases where the humidity (value of humidity) obtained by the hygrometer fluctuates due to fluctuation in the detected temperature of the outside space.

SUMMARY OF INVENTION

An object of the present invention is to provide a hygrometer that can measure the humidity of a measurement space with high precision and a temperature-humidity chamber provided with the hygrometer.

The inventor of the present invention has taken note of the following finding in order to achieve the object.

This finding relates to the heat balance in a heat transfer section. Specifically, the finding relates to the heat balance when dew formation has occurred in a portion, of the heat transfer section, located within a measurement space, in the case where heat is forcefully released from the heat transfer section such that the amount of heat release is made constant. When dew formation has occurred in this manner, a heat balance holds in which the total amount of heat of sensible heat entering the heat transfer section from the measurement space and latent heat supplied to the heat transfer section by the dew formation equals the amount of heat released forcefully from the heat transfer section, regardless of the temperature of the measurement space and the temperature of an outside space.

Based on this finding, the inventor of the present invention has examined the heat balance, taking note of the water vapor pressure of the measurement space. As a result, it has been found that a predetermined relational expression holds between the temperature of the heat transfer section as well as the temperature of the measurement space and the water vapor pressure of the measurement space, regardless of the temperature of the outside space. The humidity (relative humidity) is a partial pressure of the water vapor pressure with respect to the saturated water vapor pressure. Therefore, if the water vapor pressure and temperature of the measurement space are obtained, the humidity (relative humidity) of the measurement space can be obtained easily from the water vapor pressure and temperature.

The present invention has been made by taking note of the relational expression between the respective temperatures and the water vapor pressure of the measurement space. A hygrometer according to one aspect of the present invention is a hygrometer that measures a humidity of a measurement space, including a heat transfer section extending from the measurement space toward an outside space separated from the measurement space by a thermal insulation section, a heat release amount control unit that causes heat to be released to the outside space from the heat transfer section such that an amount of heat released to the outside space is made constant, and a computation device that calculates a humidity of the measurement space. The computation device calculates a humidity of the measurement space from a temperature of the heat transfer section and a temperature of the measurement space using a relational expression based on a heat balance in the heat transfer section when dew formation is occurring in a portion located within the measurement space in a state where the amount of heat released to the outside space from the heat transfer section is made constant by the heat release amount control unit.

A temperature-humidity chamber according to another aspect of the present invention includes a thermal insulation section that surrounds a predetermined measurement space, the hygrometer that measures a humidity of the measurement space, and a temperature and humidity adjustment section that adjusts at least one of a humidity and a temperature within the measurement space on the basis of a result of measurement by the hygrometer.

A hygrometer according to another aspect of the present invention is a hygrometer that measures a humidity within a space, including a heat transfer section extending from a first end section arranged in a first position within the space up to a second end section arranged in a second position that is apart from the first position, and capable of heat transport of heat that has entered the first end section from the space to the second end section, a heat release amount control unit that causes heat to be released to the space from the second end section of the heat transfer section such that an amount of heat released to the space is made constant, and a computation device that calculates a humidity of the space. The computation device is configured to calculate a humidity of the space from a temperature of the heat transfer section and a temperature of the space using a relational expression based on a heat balance in the heat transfer section when dew formation is occurring at least in the first end section in a state where the amount of heat released to the space from the second end section is made constant by the heat release amount control unit.

DESCRIPTION OF EMBODIMENTS

Embodiments of the present invention will be described below with reference to the accompanying drawings.

<First Embodiment>

Figure 1:
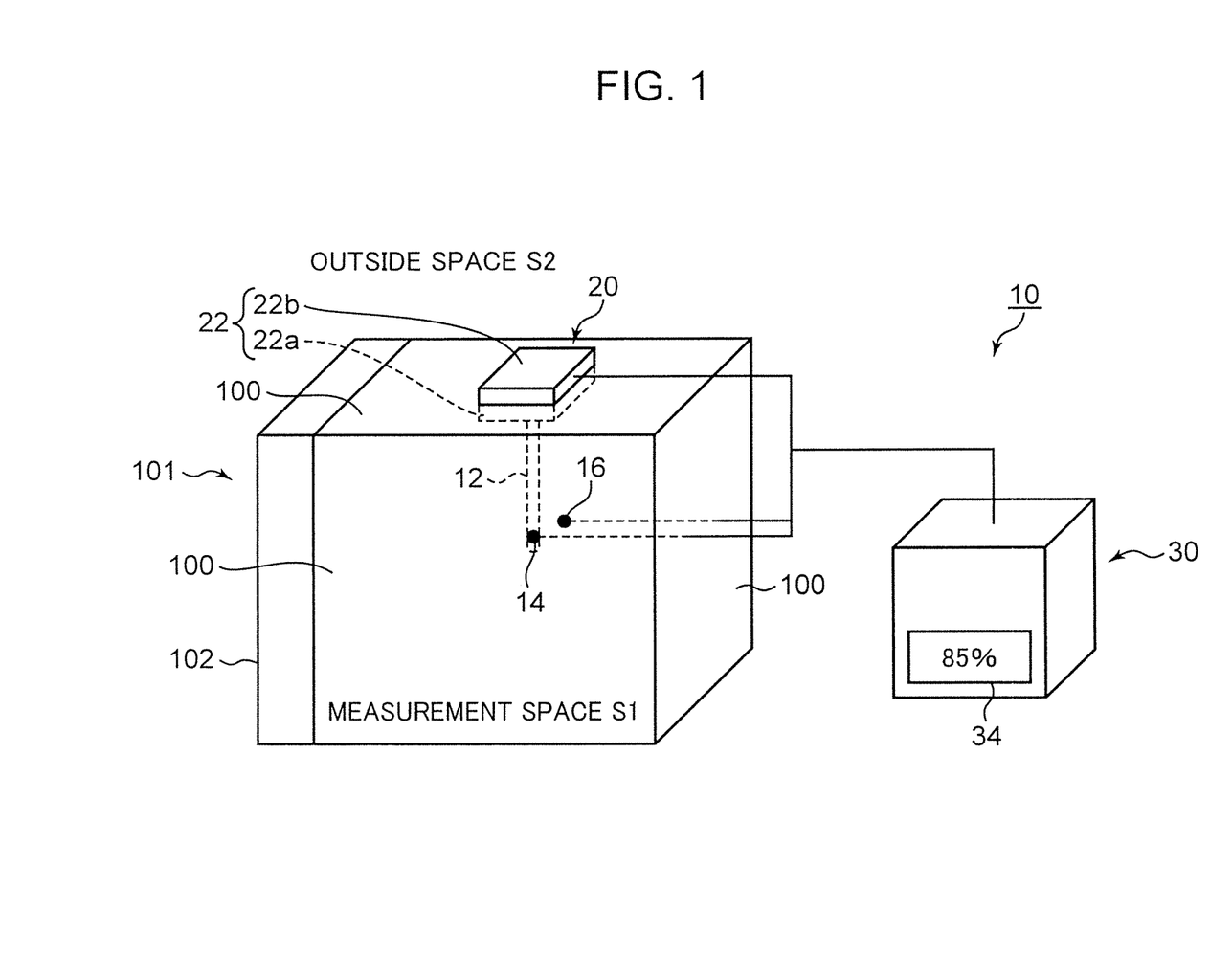
FIG. 1 is a schematic configuration diagram of a hygrometer according to a first embodiment of the present invention.
Figure 2:
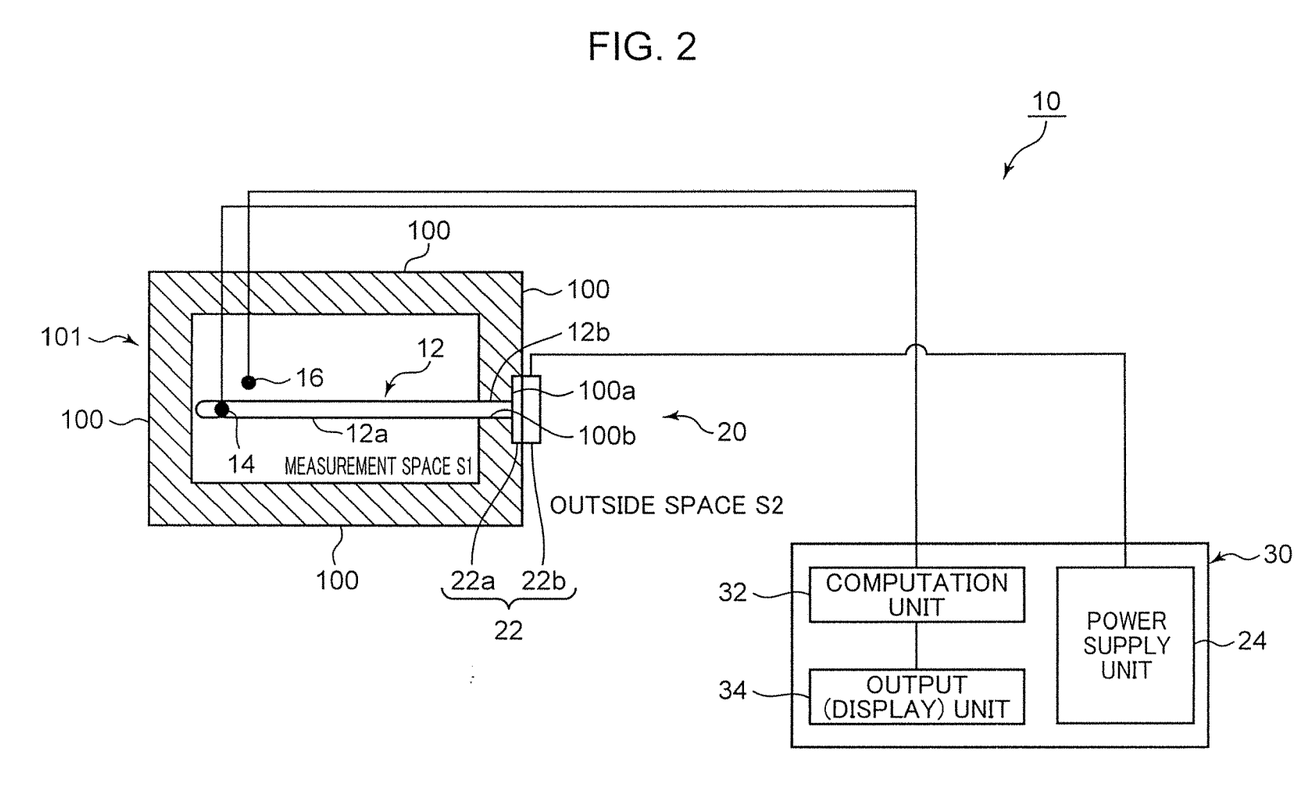
FIG. 2 is a block diagram for illustrating the function of the hygrometer.
Figure 3:
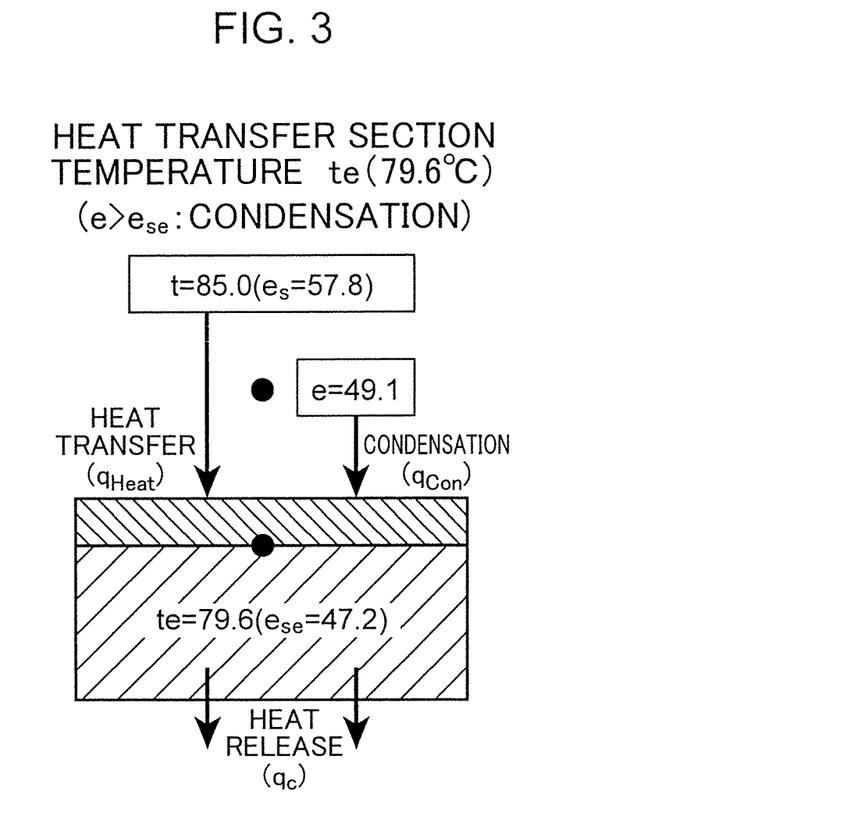
FIG. 3 is a conceptual diagram for illustrating the heat balance in a heat transfer section of the hygrometer.

FIG. 1 is a diagram schematically showing the structure of a temperature-humidity chamber provided with a hygrometer according to a first embodiment of the present invention. FIG. 2 is a block diagram for illustrating the function of the hygrometer shown in FIG. 1. FIG. 3 is a conceptual diagram for illustrating the heat balance in a heat transfer section of the hygrometer shown in FIG. 1. First, referring to FIG. 1 to FIG. 3, the configuration of the hygrometer according to the first embodiment of the present invention will be described.

The hygrometer of this embodiment is for measuring the humidity (relative humidity) within a measurement space S1 and, as shown in FIG. 1 and FIG. 2, includes a heat transfer section 12, a heat transfer section temperature sensor (heat transfer section temperature detection unit) 14, a measurement space temperature sensor (measurement space temperature detection unit) 16, a heat release amount control unit 20 including a Peltier module (Peltier element) 22, and a hygrometer body 30.

The heat transfer section 12 is configured of a heat pipe and is configured to include therein water as working fluid in a decompressed state and to generate and obtain a heat pipe phenomenon. The heat pipe phenomenon refers to a phenomenon in which the included working fluid repeats evaporation and condensation in a predetermined location, such that heat is transported along with the flow of working fluid from where evaporation of the working fluid takes place to where condensation takes place.

The heat transfer section 12 extends from the measurement space S1 toward an outside space S2 outside the measurement space S1.

The measurement space S1 is, for example, space inside a temperature-humidity chamber 101 surrounded by a thermal insulation wall 100 (thermal insulation section). The outside space S2 is space outside the temperature-humidity chamber 101. That is, the temperature-humidity chamber 101 includes a hygrometer 10.

Specifically, the temperature-humidity chamber 101 includes the thermal insulation wall (thermal insulation section) 100 surrounding the measurement space S1, the hygrometer 10, and a temperature and humidity adjustment section 102 and can control the temperature and humidity of the measurement space S1 (specifically, air within the measurement space S1). At the thermal insulation wall 100 forming a ceiling section of the temperature-humidity chamber 101, a recess section 100a that is recessed toward the measurement space S1 from the outside space S2 is formed. In the recess section 100a, the Peltier module 22 of the heat release amount control unit 20 is fitted. At a bottom section of the recess section 100a, a through hole 100b that connects the measurement space S1 and the outside space S2 is provided.

Based on the result of measurement by the hygrometer 10, the temperature and humidity adjustment section 102 adjusts at least one of a temperature (measurement space temperature) t and a humidity U within the measurement space S1.

An end section 12b on one side of the heat transfer section 12 is inserted to the through hole 100b. The heat transfer section 12 is connected with the Peltier module 22 fitted in the recess section 100a to be capable of heat transfer (heat exchange). A portion 12a on the other end section side of the heat transfer section 12 is located (exposed) within the measurement space S1. Hereinafter, a portion of the heat transfer section 12 located within the measurement space S1 is referred to as the inside portion 12a. Aside from being arranged in a perpendicular and upright posture, the heat transfer section 12 may be arranged in an inclined posture or may be arranged in a horizontal posture, as long as generating the heat pipe phenomenon is possible.

Although the heat pipe is used as the heat transfer section 12 in this embodiment, this is not limiting. For example, the heat transfer section 12 may be a solid rod body formed of copper or the like. That is, it suffices that the heat transfer section 12 be configured such that the thermal resistance upon movement of heat along the surface of the heat transfer section 12 or inside the heat transfer section 12 is extremely small compared to the thermal resistance upon entrance of heat to the heat transfer section 12 from the measurement space S1 and the thermal resistance upon release of heat to the outside space S2 from the heat transfer section 12 by the heat release amount control unit 20.

The heat transfer section temperature sensor 14 is a sensor that detects a temperature (heat transfer section temperature) to of the heat transfer section 12 used in computation for obtaining the relative humidity U. The heat transfer section temperature sensor 14 of this embodiment detects the outer surface (surface) temperature of the heat transfer section 12 and outputs a signal in accordance with the detection result. Specifically, the heat transfer section temperature sensor 14 is attached to the outer surface near an end section of the inside portion 12a located within the measurement space S1. The heat transfer section temperature sensor 14 may be not arranged to contact the outer surface of the heat transfer section 12 (inside portion 12a). That is, the heat transfer section temperature sensor 14 may be of a configuration in which the temperature of the heat transfer section 12 is measured in a contactless manner or may be of a configuration in which the temperature of the heat transfer section 12 is measured in a state of being embedded within the heat transfer section 12. The heat transfer section temperature sensor 14 may be arranged to contact the inner surface of the heat pipe, in the case where the heat transfer section 12 is configured of the heat pipe.

The measurement space temperature sensor 16 is a sensor that detects the temperature (measurement space temperature) t of the measurement space S1 used in computation for obtaining the relative humidity U. The measurement space temperature sensor 16 is arranged within the measurement space S1 to detect the temperature t within the measurement space S1 and output a signal in accordance with the detection result.

The heat release amount control unit 20 includes the Peltier module 22 and a power supply unit 24 that supplies power to the Peltier module 22. The heat release amount control unit 20 controls the amount of power supply to the Peltier module 22 from the power supply unit 24, such that the amount of heat released to the outside space S2 is made constant.

The Peltier module (Peltier element) 22 is connected to the end section 12b on the other side of the heat transfer section 12 in a state of being fitted in the recess section 100a of the temperature-humidity chamber 101. Specifically, the Peltier module 22 includes a heat absorbing portion (cooling portion) 22a and a heat releasing portion (heating portion) 22b. The heat absorbing portion 22a is connected to the end section 12b on the other side of the heat transfer section 12 in a state of being fitted in the recess section 100a to be capable of heat exchange (capable of cooling). By the Peltier module 22 being arranged in this manner, a portion of the heat transfer section 12 other than the inside portion 12a is surrounded by the thermal insulation wall (thermal insulation section) 100 and the Peltier module 22. In this manner, one end section (end section 12b on the other side) of the heat transfer section 12 is not exposed to the outside space S2, and the arrangement is such that heat can be released from one end section of the heat transfer section 12 to the outside space S2 only through the Peltier module 22 (in a state where heat cannot be released directly from the heat transfer section 12 to the outside space S2). Therefore, control of the amount of heat released to the outside space S2 from the heat transfer section 12 can be performed easily. That is, the hygrometer 10 of this embodiment controls the amount of heat released to the outside space S2 from the heat transfer section 12 through the Peltier module 22 by controlling power supplied to the Peltier module 22.

In the Peltier module 22, the heat absorbing portion 22a absorbs heat from the end section 12b on the other side of the heat transfer section 12 (i.e., cools the end section 12b on the other side) when power is supplied from the power supply unit 24, and the heat releasing portion 22b releases the heat to the outside space S2. At this time, in the heat transfer section 12, working fluid evaporates within the inside portion 12a, and working fluid in a gaseous state condenses within the end section 12b on the other side. Accordingly, heat that has entered the inside portion 12a of the heat transfer section 12 from the measurement space S1 moves to the end section 12b on the other side and is transferred to the Peltier module 22.

The power supply unit 24 is capable of supplying constant power with respect to the Peltier module 22. Although arranged inside the hygrometer body 30 in this embodiment, the power supply unit 24 may be provided separately from the hygrometer body 30 without being limited to this arrangement.

By the power supply unit 24 supplying constant power (e.g., applying constant voltage or supplying constant current) with respect to the Peltier module 22, the amount of heat released to the outside space S2 from the heat transfer section 12 through the Peltier module 22 is made constant.

The hygrometer body 30 calculates the humidity U within the measurement space S1 and displays (outputs) the calculated humidity U. The hygrometer body 30 includes a computation unit (computation device) 32 that calculates the relative humidity U, an output unit 34 that externally outputs the computation result of the computation unit 32, and the power supply unit 24. The hygrometer body 30 of this embodiment is connected with the respective sensors 14 and 16 to be detachable.

The computation unit 32 receives a signal from the respective sensors 14 and 16 and calculates the humidity U. Specifically, the computation unit 32 calculates the relative humidity U of the measurement space S1 using the heat transfer section temperature te detected by the heat transfer section temperature sensor 14 and the measurement space temperature t detected by the measurement space temperature sensor 16. Specifically, the following expression (1) (predetermined relational expression) and the following expression (2) are stored in the computation unit 32 in advance, and the computation unit 32 calculates the relative humidity U of the measurement space S1 from the heat transfer section temperature te and the measurement space temperature t using the expression (1) and expression (2).

[Math. 1]
$$e = e_{se} + A \cdot p \cdot (t - t_e) + A \cdot \frac{\delta \cdot p \cdot q_c}{\lambda} \quad (1)$$

[Math. 2]
$$U(\%) = \frac{e}{e_s} \times 100 \quad (2)$$

Herein, A in expression (1) is the coefficient, t is the measurement space temperature (temperature of air within the measurement space S1), $t_e$ is the heat transfer section temperature (surface temperature of the heat transfer section 12), $e_{se}$ is the saturated water vapor pressure at the heat transfer section temperature $t_e$, p is the pressure of the measurement space S1, $\delta$ is the boundary film thickness, and $q_C$ is the amount of heat release from the heat transfer section 12 to the outside space S2. Also, $e_s$ in expression (2) is the saturated water vapor pressure at the measurement space temperature t.

Specifically, the computation unit 32 first calculates a water vapor pressure (water vapor partial pressure) e of the measurement space S1 from the heat transfer section temperature te and the measurement space temperature t using expression (1). Subsequently, the computation unit 32 calculates the humidity U of the measurement space S1 from the water vapor pressure e and the saturated water vapor pressure es at the measurement space temperature t using expression (2). The saturated water vapor pressure es used at this time is read by the computation unit 32 from data stored in a table stored in the computation unit 32 in advance. The table stores, for example, data in which the temperature and the saturated water vapor pressure at each temperature are associated.

Expression (1) is an expression based on the heat balance in the heat transfer section 12 in the case of a state where heat is forcefully released from the heat transfer section 12 to the outside space S2 such that the amount of heat qC released to the outside space S2 is made constant, the state being such that dew formation is occurring on the inside portion 12a. The expression (1) is obtained as follows.

When heat is forcefully released to the outside space S2 from the heat transfer section 12 such that the amount of heat qC released to the outside space S2 is made constant, heat is transported toward the outside space S2 side (end section 12b on the other side) from the measurement space S1 side by the working fluid within the heat transfer section 12. Accordingly, the heat transfer section temperature te becomes less than or equal to the dew point of the measurement space S1, and dew formation occurs on the inside portion 12a of the heat transfer section 12. Assuming latent heat supplied to the heat transfer section 12 from the measurement space S1 by dew formation at this time as qCon and sensible heat entering the heat transfer section 12 from the measurement space S1 as $q_{Heat}$, the latent heat $q_{Con}$ and the sensible heat $q_{Heat}$ are represented respectively with the following expression (3-1) and expression (3-2).

[Math. 3]

$$q_{Con} = -H_v \cdot \frac{D}{\delta} \cdot \frac{p_0}{p} \cdot \frac{1}{R \cdot t_e}(e_{se} - e) \quad (3\text{-}1)$$

$$q_{Heat} = -\frac{\lambda}{\delta}(t - t_e) \quad (3\text{-}2)$$

In expression (3-1) and expression (3-2), $H_v$ is the latent heat of water, D is the water vapor diffusion coefficient, $P_0$ is the atmospheric pressure, R is the gas constant, and λ is the thermal conductivity of air.

Assume that dew formation has occurred on the inside portion 12a of the heat transfer section 12, in the case where heat is forcefully released to the outside space S2 from the heat transfer section 12 such that the amount of heat qC released to the outside space S2 is made constant. At this time, the following heat balance holds regardless of the relative humidity U of the measurement space S1 and the temperature of the outside space S2. The heat balance is a heat balance in which the total amount of heat of the sensible heat qHeat that enters the heat transfer section 12 from the measurement space S1 and the latent heat qCon supplied to the heat transfer section 12 by the dew formation equals the amount of heat qC forcefully released to the outside space S2 from the heat transfer section 12.

Thus, a relationship represented by the following expression (4) holds for $q_{Con}$, $q_{Heat}$, and $q_C$ (see FIG. 3).

[Math. 4]

$$q_c = q_{Con} + q_{Heat} \quad (4)$$

Through substitution of the expression (3-1) and expression (3-2) into expression (4) and simplification, relational expression (5) for obtaining the water vapor pressure e of air within the measurement space S1 holds.

[Math. 5]

$$e = e_{se} + \left[\frac{R \cdot t_e \cdot \lambda}{H_v \cdot D \cdot p_0}\right] \cdot p \cdot (t - t_e) + \left[\frac{R \cdot t_e \cdot \lambda}{H_v \cdot D \cdot p_0}\right] \cdot \frac{p \cdot \delta \cdot q_c}{\lambda} \quad (5)$$

By replacing an expression enclosed in a dotted line in the second term and an expression enclosed in a dotted line in the third term in the expression (5) respectively with a coefficient A, the expression (1) can be obtained.

The output unit 34 outputs the relative humidity U of the measurement space S1 from the computation result of the computation unit 32. The output unit 34 of this embodiment is configured to display the computation result. The output unit 34 is not limited to the configuration of displaying the computation result. For example, the output unit may be configured to output a signal for displaying the computation result or the like in an external display device or the like such as a liquid crystal display. The output unit may be configured such that output is through printing or the like.

In the hygrometer 10 configured in this manner, the humidity U of the measurement space S1 is measured in the following manner.

First, when the hygrometer body 30 is activated, the power supply unit 24 supplies constant power to the Peltier module 22. In this embodiment, the power supply unit 24 supplies constant current with respect to the Peltier module 22. Accordingly, the amount of heat release qC from the heat transfer section 12 to the outside space S2 through the Peltier module 22 can be made constant. As a result, the temperature of the inside portion 12a of the heat transfer section 12 decreases and becomes less than or equal to the dew point temperature of the measurement space S1. Accordingly, condensation occurs in the inside portion 12a. When this state continues for a predetermined time, the temperature of the heat transfer section 12 comes to an equilibrium state and become stabilized.

Subsequently, the computation unit 32 receives a signal showing the detection result of the heat transfer section temperature sensor 14 (i.e., signal representing the heat transfer section temperature te) and a signal showing the detection result of the measurement space temperature sensor 16 (i.e., signal representing the measurement space temperature t). The computation unit 32 substitutes the respective temperatures represented by the respective signals from the respective sensors 14 and 16 into expression (1) for computation and accordingly calculates the water vapor pressure e of the measurement space S1.

For example, in an example shown in FIG. 3, a case where the heat transfer section temperature te is 79.6° C., the measurement space temperature t is 85.0° C., and the amount of heat (amount of heat release) released to the outside space S2 from the heat transfer section 12 by the Peltier module 22 is 20336 W/m2 is shown. At this time, the computation unit 32 obtains the water vapor pressure e by substituting these values into expression (1). Subsequently, when the water vapor pressure e of the measurement space S1 is calculated, the computation unit 32 substitutes the water vapor pressure e (e=49.1 in the example shown in FIG. 3) and the saturated water vapor pressure es at the measurement space temperature t detected by the measurement space temperature sensor 16 respectively into expression (2) to compute the relative humidity U.

[Math. 6]

$$U(\%) = \frac{e}{e_s} = \frac{49.1}{57.8} \times 100 = 85(\%) \quad (6)$$

The relative humidity U (85% in the example) of the measurement space S1 thus obtained is output to the output unit 34 by the computation unit 32. The output unit 34 displays (outputs) the relative humidity U of the measurement space S1 calculated by the computation unit 32.

With the hygrometer 10 described above, dew formation is generated in the portion 12a located within the measurement space S1 of the heat transfer section 12 by releasing heat forcefully to the outside space S2 from the heat transfer section 12 such that the released amount of heat (amount of heat release to the outside space S2 from the heat transfer section 12) qC is made constant. On that basis, the humidity of the measurement space S1 is derived using expression (1). Therefore, the humidity U of the measurement space S1 can be obtained with high precision without being influenced by the temperature of the outside space S2.

Specifically, the humidity U is obtained with expression (1) and expression (2) in which the temperature of the outside space S2 is not used as a parameter. Accordingly, the influence of the temperature of the outside space S2 can be prevented in the calculation of the humidity U. Moreover, since heat is released forcefully to the outside space S2 from the heat transfer section 12 such that the amount of heat release qC is made constant (a predetermined value), the temperature of the heat transfer section 12 is stabilized without being influenced by the temperature of the outside space S2 and fluctuation thereof. Therefore, the hygrometer 10 can obtain the humidity of the measurement space S1 with high precision without being influenced by the temperature of the outside space S2 and fluctuation thereof, regardless of the temperature (heat transfer section temperature) of the heat transfer section 12 that releases heat to the outside space S2 is used as a parameter in expression (1).

Since the hygrometer 10 does not require a wick as in a conventional psychrometer, workload relating to maintenance, such as replacement of a wick every time there is deterioration in suctioning of water due to aging, can be reduced. Thus, in the hygrometer 10 of this embodiment, the structure can be simplified while reducing workload relating to maintenance.

Since the outer surface (surface) temperature of the heat transfer section 12 is detected by the heat transfer section temperature sensor 14 in the hygrometer 10 of this embodiment, the structure of the heat transfer section 12 and the structure of the heat transfer section temperature sensor 14 can be simplified compared to a case where the temperature of the heat transfer section 12 is detected inside the heat transfer section 12.

In the hygrometer 10 according to the first embodiment, the heat transfer section temperature sensor 14 detects the outer surface (surface) temperature of the inside portion 12a (near the end section on the measurement space S1 side in this embodiment). However, the position in which the heat transfer section temperature to te is detected by the heat transfer section temperature sensor 14 is not limited to this position. For example, the heat transfer section temperature sensor 14 may be arranged to detect the surface temperature of the heat transfer section 12 within the thermal insulation wall 100. Since the outer surface (surface) temperature of the heat transfer section 12 is easily influenced by disturbance such as wind, the heat transfer section temperature sensor 14 may be arranged in a position within the thermal insulation wall 100 where influence of wind or the like is less likely. In this case, an error in the obtained humidity U due to disturbance can be prevented by calculating the humidity U using the temperature measured by the heat transfer section temperature sensor 14.

<Second Embodiment>

Figure 4:
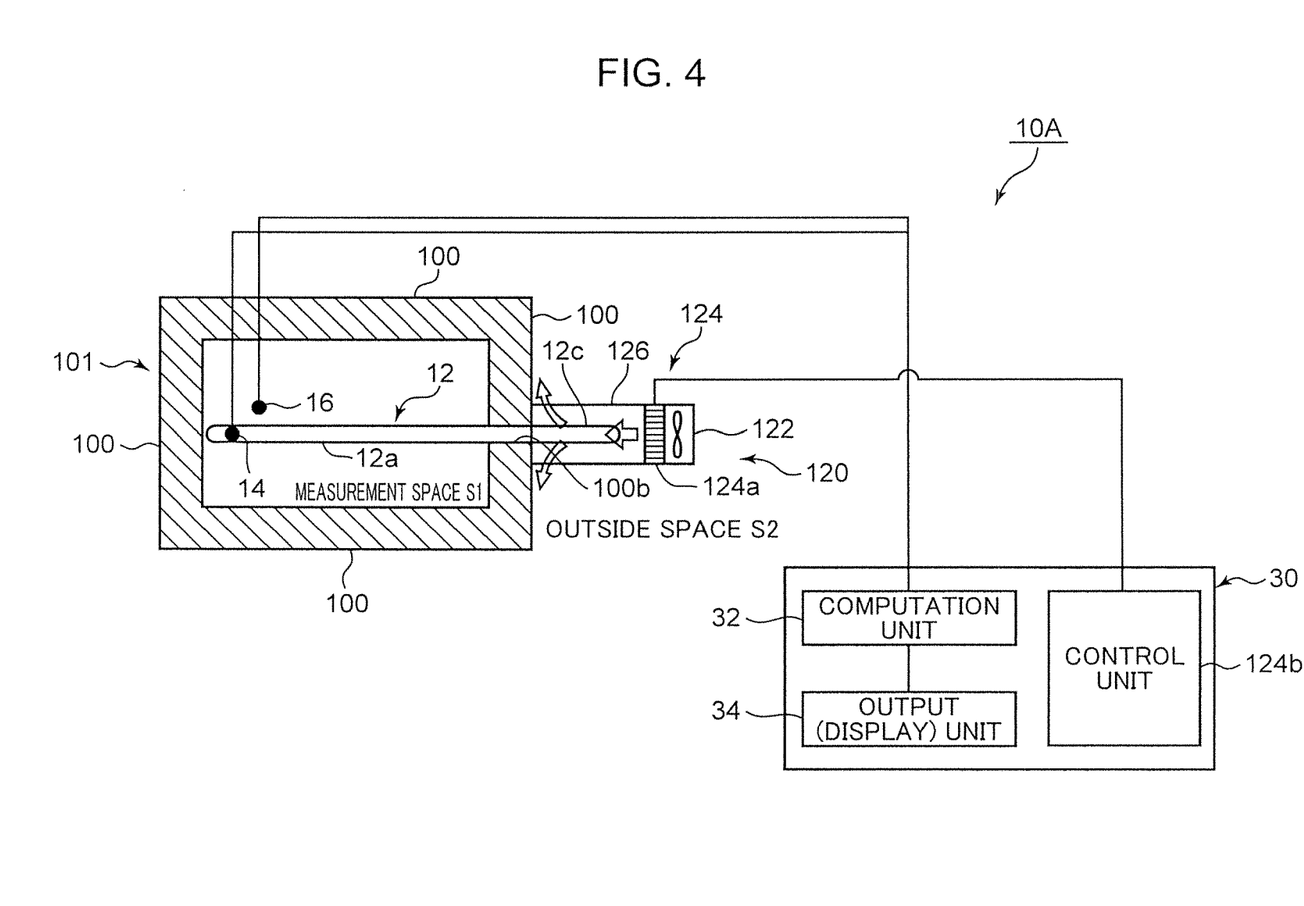
FIG. 4 is a schematic configuration diagram of a hygrometer according to a second embodiment of the present invention.

A second embodiment of the present invention will be described with reference to FIG. 4. In the second embodiment, the same reference numerals are used and description is omitted for configurations similar to the first embodiment. Only different configurations will be described.

A hygrometer 10A of the second embodiment differs from the hygrometer 10 of the first embodiment in the arrangement of the heat transfer section 12 and the configuration of a heat release amount control unit 120.

The heat transfer section 12 is arranged to penetrate the thermal insulation wall 100. That is, the heat transfer section 12 is arranged across the measurement space S1 and the outside space S2 outside the measurement space S1. Thus, one end section of the heat transfer section 12 is located within the measurement space S1, and the other end section of the heat transfer section 12 is located within the outside space S2. Hereinafter, a portion of the heat transfer section 12 located within the outside space S2 is assumed as an outside portion 12c.

The heat release amount control unit 120 includes an air supply section 122, a temperature adjustment section 124, and a guide section 126.

The air supply section 122 forms a flow of air (external air) toward the outside portion (portion protruding toward the outside space S2 side) 12c of the heat transfer section 12. In this embodiment, the air supply section 122 is a blower fan. The air supply section 122 blows toward the outside portion 12c such that the air flow is made constant. The air supply section 122 of this embodiment blows in a direction toward the thermal insulation wall 100 (base end of the outside portion 12c) side from the tip end of the outside portion 12c in the protruding direction.

The temperature adjustment section 124 includes an air cooling section 124a and a control unit 124b.

The air cooling section 124a is arranged between the air supply section 122 and the outside portion 12c and adjusts the temperature of air toward the outside portion 12c from the air supply section 122. The air cooling section 124a includes a temperature sensor (omitted in the drawing) that detects the temperature of air supplied from the air supply section 122.

The control unit 124b controls the cooling performance of the air cooling section 124a on the basis of the temperature (temperature of air supplied from the air supply section 122) detected by the temperature sensor, omitted in the drawing, of the air cooling section 124a. By the cooling performance of the air cooling section 124a being adjusted, the temperature of air supplied to the outside portion 12c is held constant.

With the hygrometer 10A described above as well, heat can be released forcefully to the outside space S2 from the heat transfer section 12 such that the released amount of heat (amount of heat release from the heat transfer section 12 to the outside space S2) qC is made constant. Accordingly, dew formation occurs in the portion 12a of the heat transfer section 12 located within the measurement space, and the humidity of the measurement space S1 is derived using expression (1) and expression (2) on that basis. Therefore, the humidity U of the measurement space S1 can be obtained with high precision without being influenced by the temperature of the outside space S2.

The guide section 126 guides air after temperature adjustment by the air cooling section 124a to the outside portion 12c. By the guide section 126 guiding air after temperature adjustment, mixing of external air into the flow of air after temperature adjustment can be prevented. Accordingly, air at a constant temperature (predetermined temperature) reaches the outside portion 12c with a constant air flow. Then, air that has received heat from the outside portion 12c is released to the outside space S2 from an end section opening of the guide section 12b on the thermal insulation wall 100 side.

Other configurations, operations, and effects of which description is omitted are similar to the first embodiment.

<Third Embodiment>

Figure 5:
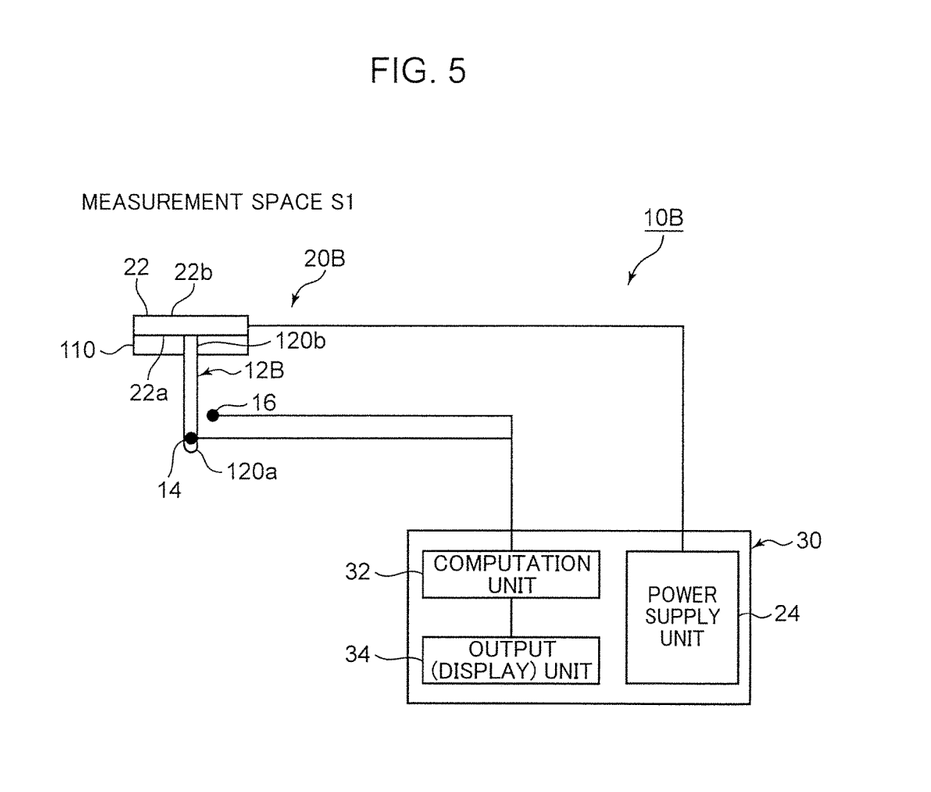
FIG. 5 is a schematic configuration diagram of a hygrometer according to a third embodiment of the present invention.

A third embodiment of the present invention will be described with reference to FIG. 5. In the third embodiment, the same reference numerals are used and description is omitted for configurations similar to the first and second embodiments. Only different configurations will be described.

With a hygrometer 10B of the third embodiment, it is possible to arrange the entire configuration of the hygrometer 10B within one space (measurement space) S1, unlike the hygrometers 10 and 10A of the first and second embodiments. That is, with the hygrometer 10B of the third embodiment, the humidity of the measurement space S1 can be measured without releasing heat of a heat transfer section 12B to a space (outside space in the first and second embodiments) separated from the space (measurement space) S1 of which humidity is to be measured. In other words, with the hygrometer 10B of the third embodiment, the humidity of the measurement space S1 can be measured while releasing heat of the heat transfer section 12 within the measurement space S1.

The heat transfer section 12B has a shape extending from a first end section 120a up to a second end section 120b and is capable of transporting heat that has entered the first end section 120a from the measurement space S1 up to the second end section 120b. In the third embodiment, the heat transfer section 12B is a heat pipe in a similar manner to the first embodiment. The heat transfer section 12B of the third embodiment is shorter than the heat transfer section 12 of the first and second embodiments. The reason is as follows. Since the difference of the temperature of the heat transfer section 12B and the temperature of the measurement space S1 is small, the amount of heat releasable from the second end section 120b of the heat transfer section 12B to the measurement space S1 by a heat release amount control unit 20B (specifically, Peltier module 22) is small in the third embodiment. Therefore, by reducing the surface area of a portion (portion on the lower end side relative to a thermal insulation member 110 in FIG. 5) of the heat transfer section 12B where heat (sensible heat) from the measurement space S1 enters, condensation can be generated more easily in the portion even if the amount of heat release from the second end section 120b is small. Thus, the heat transfer section 12B of the third embodiment is shorter than the heat transfer section 12 of the first and second embodiments. Accordingly, the measurement range of the hygrometer 10B is increased.

The heat transfer section 12B is arranged in a perpendicular and upright posture. This is because, in the case where the heat transfer section 12B is configured of the heat pipe as in this embodiment, the thermal resistance of the heat pipe is reduced by the heat pipe being arranged in the upright posture, and the amount of heat release from the second end section 120b can be increased accordingly. As a result, it becomes easier for condensation to occur in a portion on the first end section 120a side, even if the amount of heat releasable by the Peltier module 22 is small as in this embodiment.

The heat release amount control unit 20B includes the thermal insulation member 110, aside from the Peltier module 22 and the power supply unit 24.

The thermal insulation member 110 is arranged to surround the second end section 120b of the heat transfer section 12B. The thermal insulation member 110 causes a heat pipe phenomenon to occur more easily in the heat transfer section 12B. As described above, the heat pipe phenomenon refers to a phenomenon in which included working fluid repeats evaporation and condensation in a predetermined location, such that heat is transported along with the flow of working fluid from where evaporation of the working fluid takes place to where condensation takes place. The thermal insulation member 110 is preferably provided so that heat transport in the heat transfer section 12B is performed more easily, but is not mandatory.

The measurement space temperature sensor 16 is arranged in a position within the measurement space S1 that is not influenced by heat release from the heat release amount control unit 20B (heat releasing portion 22b of the Peltier module 22).

In the hygrometer 10B with the configuration described above, heat is released forcefully to the measurement space S1 from the second end section 120b of the heat transfer section 12B, such that the released amount of heat (amount of heat release to the measurement space S1 from the heat transfer section 12B) is made constant. Accordingly, condensation occurs at least in the first end section 120a of the heat transfer section 12B. By the humidity U being computed using expression (1) and expression (2), the humidity U of a space at each temperature t can be obtained with high precision, even if the measurement space temperature t fluctuates.

Other configurations, operations, and effects of which description is omitted are similar to the first and second embodiments.

EXAMPLE

Results of measuring the humidity of a measurement space with the hygrometer of the first embodiment and a hygrometer as a comparative example will be shown below. In the hygrometer as the comparative example, a heat transfer section is arranged across the measurement space and an outside space. With the hygrometer of the comparative example, the humidity of the measurement space is obtained by computation from the temperature of the heat transfer section, the temperature of the measurement space, and the temperature of the outside space that are detected in a state where condensation has occurred in a portion, of the heat transfer section, located within the measurement space. In the comparative example as well, a heat pipe is used as the heat transfer section.

Figure 6A:
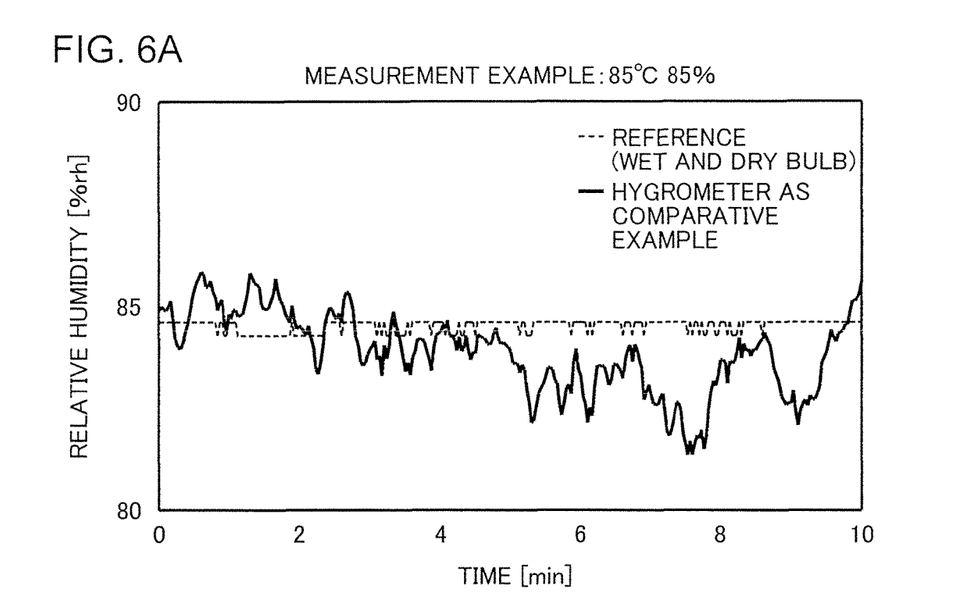
FIG. 6A is a diagram showing one example of a result of measurement by a psychrometer and a hygrometer as a comparative example when a measurement space is in a high-temperature and high-humidity state (state where the temperature is 85° C. and the humidity is 85%)
Figure 6B:
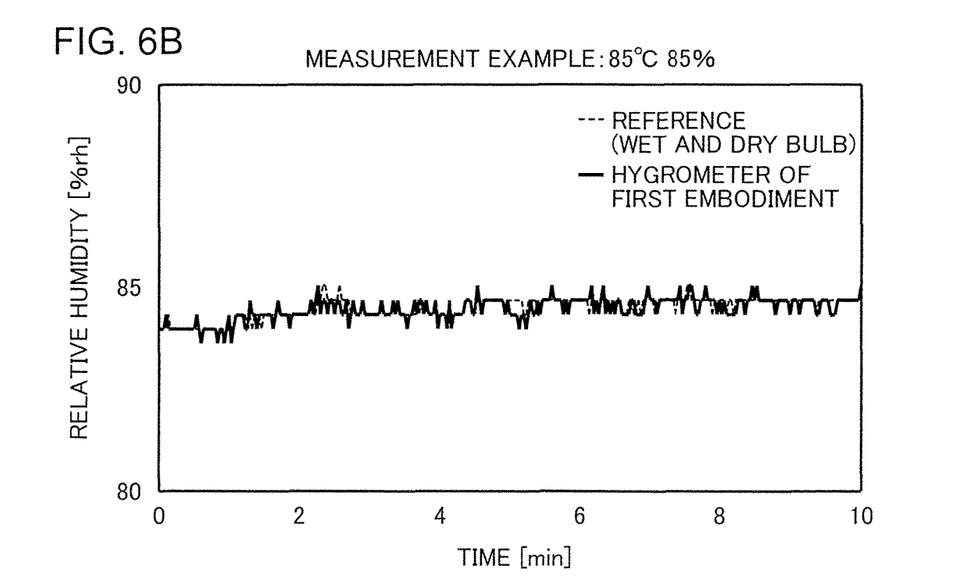
FIG. 6B is a diagram showing one example of a result of measurement by a psychrometer and the hygrometer of the first embodiment when a measurement space is in a high-temperature and high-humidity state (state where the temperature is 85° C. and the humidity is 85%).
Figure 7A:
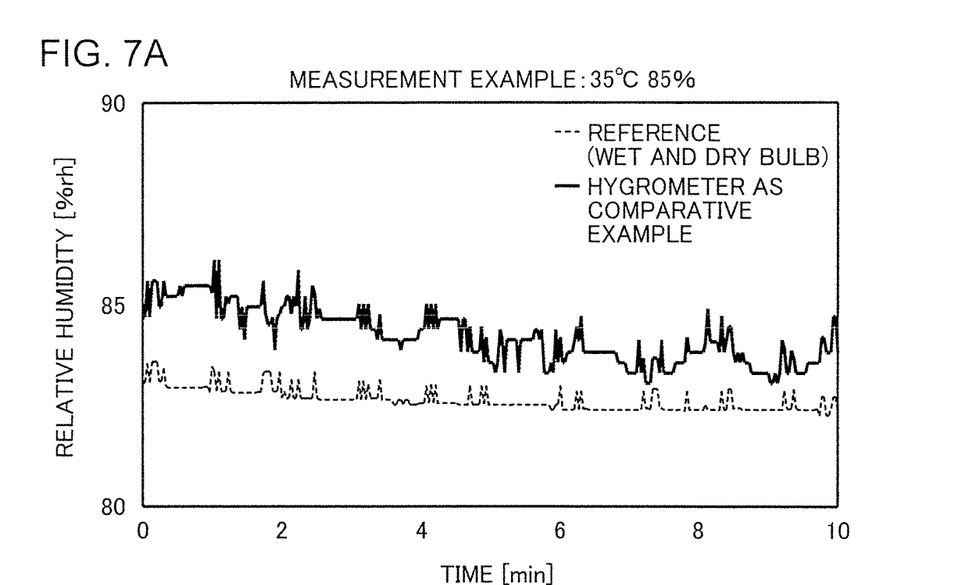
FIG. 7A is a diagram showing one example of a result of measurement by a psychrometer and a hygrometer as a comparative example when a measurement space is in a low-temperature and high-humidity state (state where the temperature is 35° C. and the humidity is 85%)
Figure 7B:
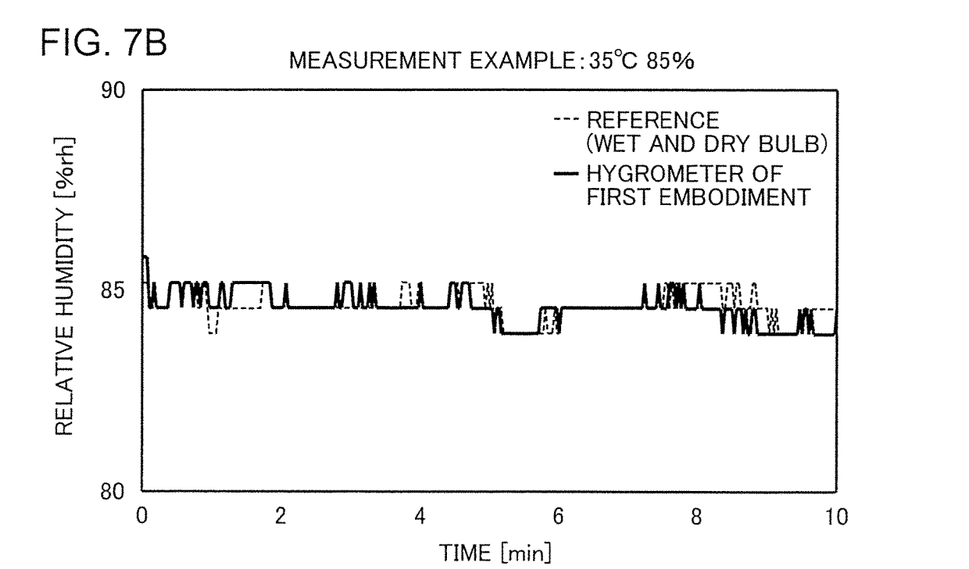
FIG. 7B is a diagram showing one example of a result of measurement by a psychrometer and the hygrometer of the first embodiment when a measurement space is in a low-temperature and high-humidity state (state where the temperature is 35° C. and the humidity is 85%).

FIG. 6A shows the result of measurement by a psychrometer (broken line) and the result of measurement by the hygrometer as the comparative example (solid line) when the measurement space is in a high-temperature and high-humidity state (e.g., state where the temperature is 85° C. and the humidity is 85%). FIG. 6B shows the result of measurement by a psychrometer (broken line) and the result of measurement by the hygrometer of the first embodiment (solid line) when the measurement space is in a high-temperature and high-humidity state (e.g., state where the temperature is 85° C. and the humidity is 85%). FIG. 7A shows the result of measurement by a psychrometer (broken line) and the result of measurement by the hygrometer as the comparative example (solid line) when the measurement space is in a low-temperature and high-humidity state (e.g., state where the temperature is 35° C. and the humidity is 85%). FIG. 7B shows the result of measurement by a psychrometer (broken line) and the result of measurement by the hygrometer of the first embodiment (solid line) when the measurement space is in a low-temperature and high-humidity state (e.g., state where the temperature is 35° C. and the humidity is 85%).

From comparison of FIG. 6A and FIG. 6B and comparison of FIG. 7A and FIG. 7B, it has been confirmed that a stable value (measurement value) with little fluctuation in the value of the measurement result (vertical fluctuation in the graph) is obtained with the hygrometer of the first embodiment compared to the hygrometer as the comparative example. That is, it has been confirmed that the humidity of the measurement space can be measured with high precision with the hygrometer of the first embodiment, compared to the hygrometer as the comparative example in which external air temperature is used in computation for obtaining the humidity.

From comparison of the waveform shown by the solid line and the waveform shown by the broken line in FIG. 6B and FIG. 7B, it has been confirmed that the hygrometer of the first embodiment can measure the humidity of the measurement space with high precision in a similar manner to the psychrometer.

The hygrometer of the present invention is not limited to the first to third embodiments, and various changes may obviously be applied without departing from the gist of the present invention.

The specific configuration of the heat release amount control unit is not limited to the respective embodiments. For example, the amount of heat release to the outside space S2 (or measurement space S1) from the heat transfer section 12 is held constant by the Peltier module 22 in the heat release amount control unit 20 of the first (or third) embodiment, and the amount of heat release to the outside space S2 from the heat transfer section 12 is held constant by blowing temperature-adjusted air in the heat release amount control unit of the second embodiment. However, these are not limiting. For example, the configuration of the heat release amount control unit may be such that heat is releasable to the outside space S2 from the heat transfer section 12 such that the amount of heat release is made constant, using a cooling device other than the Peltier module 22 or temperature-adjusted water (fluid).

In the hygrometer 10 of the first embodiment, one end section 12b of the heat transfer section 12 is not exposed to the outside space S2, since one end section 12b of the heat transfer section 12 is surrounded by the thermal insulation wall 100 and the Peltier module 22. However, the configuration is not limiting. For example, the configuration may be such that a part of the heat transfer section 12 is exposed to the outside space S2, as long as the configuration allows the total amount of heat of the amount of heat released to the outside space S2 from a portion of the heat transfer section 12 exposed to the outside space S2 and the amount of heat released to the outside space S2 from the heat transfer section 12 by the Peltier module 22 to be held constant. Alternatively, the configuration may be such that a part of the heat transfer section 12 is exposed to the outside space S2, even in the case of a configuration in which the amount of heat released to the outside space S2 from a portion exposed to the outside space S2 falls under a range of error.

The computation unit 32 of the first to third embodiments stores expression (1) and expression (2) in advance and calculates the humidity using these expressions. However, the configuration is not limiting. For example, it may be such that each measurement space temperature t and the relative humidity U with respect to each heat transfer section temperature to are respectively obtained from expression (1) and expression (2), a table in which the measurement space temperature t, each heat transfer section temperature te, and the humidity U are associated is created, and this is stored in the computation unit 32 in advance. In this case, the computation unit 32 obtains the humidity U using the table.

In the hygrometers 10, 10A, and 10B of the first to third embodiments, only the relative humidity U of the measurement space S1 is derived. However, the configuration is not limiting. The hygrometer may obtain, in addition to the relative humidity U, the dew point of the measurement space S1 from the obtained relative humidity U and the detected measurement space temperature t.

The hygrometers 10, 10A, and 10B of the first to third embodiments include the heat transfer section temperature sensor 14 and the measurement space temperature sensor 16. However, the configuration is not limiting. The computation unit of the hygrometer may be configured to calculate the humidity U using the heat transfer section temperature te and the measurement space temperature t input from another instrument.

With the hygrometer 10B of the third embodiment, heat is released to the measurement space S1 with a constant amount of heat release from the second end section 120b of the heat transfer section 12B using the Peltier module 22. However, the configuration is not limiting. For example, heat may be released from the second end section 120b of the heat transfer section 12B using the air supply section 122, the temperature adjustment section 124, and the guide section 126 as in the hygrometer 10A of the second embodiment. In this case, the air supply section, the temperature adjustment section, and the guide section are arranged or configured such that the flow of air caused by the air supply section does not come into contact with a humidity measurement portion of the heat transfer section 12B (i.e., portion of the heat transfer section 12B where heat of the measurement space S1 enters the heat transfer section 12B).

The heat transfer sections 12 and 12A of the first to third embodiments both extend straight, but may be curved or bent along the way.

Figure 8:
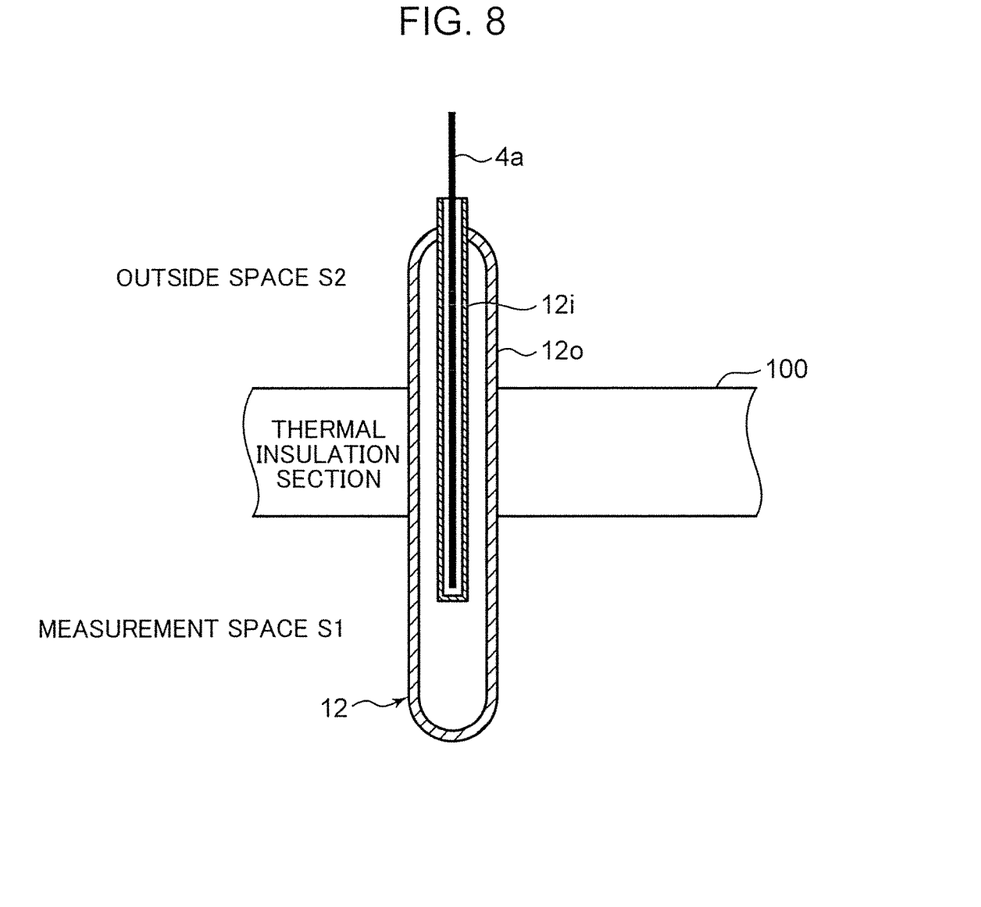
FIG. 8 is a diagram showing the schematic configuration of a heat transfer section temperature sensor in a hygrometer according to another embodiment of the present invention.

In the hygrometer of the first to third embodiments, the outer surface (surface) temperature detected by the heat transfer section temperature sensor 14 attached to the outer surface (surface) of the heat transfer section is employed as the temperature to of the heat transfer section 12. However, this is not limiting. For example, the heat transfer section temperature sensor 14 may be configured to detect the inside temperature of the heat transfer section 12. Specifically, in the case where the heat transfer section 12 is configured of a heat pipe, the heat transfer section 12 is of a double pipe structure having an inner pipe 12i and an outer pipe 12o surrounding the outside thereof, as shown in FIG. 8. In the heat transfer section 12, working fluid is included so that a heat pipe phenomenon occurs in a space between the inner pipe 12i and the outer pipe 12o. Within the inner pipe 12i, a temperature detection member (sheath thermocouple in FIG. 8) 4a of the heat transfer section temperature sensor 14 is inserted. With such a configuration, the inside temperature (temperature of a pipe wall of the inner pipe 12i) of the heat transfer section 12 can be detected. In FIG. 8, a configuration in which the heat transfer section 12 penetrates the thermal insulation wall 100 as in the second embodiment is shown. However, the configuration in which the heat transfer section temperature sensor 14 detects the inside temperature of the heat transfer section 12 may be a configuration in which one end section 12b of the heat transfer section 12 is arranged within the thermal insulation wall as in the first embodiment and the third embodiment.

SUMMARY OF EMBODIMENT

The embodiments will be summarized.

(1) The hygrometer of the embodiment is a hygrometer that measures a humidity of a measurement space, including a heat transfer section extending from the measurement space toward an outside space separated from the measurement space by a thermal insulation section, a heat release amount control unit that causes heat to be released to the outside space from the heat transfer section such that an amount of heat released to the outside space is made constant, and a computation device that calculates a humidity of the measurement space. The computation device calculates a humidity of the measurement space from a temperature of the heat transfer section and a temperature of the measurement space using a relational expression based on a heat balance in the heat transfer section when dew formation is occurring in a portion located within the measurement space in a state where the amount of heat released to the outside space from the heat transfer section is made constant by the heat release amount control unit.

With the hygrometer, heat is released forcefully to the outside space from the heat transfer section, such that the amount of heat released from the heat transfer section (amount of heat release to the outside space from the heat transfer section) is made constant. In a state where dew formation has occurred in the portion, of the heat transfer section, located within the measurement space, the humidity of the measurement space is derived using the relational expression. Therefore, the humidity of the measurement space can be obtained with high precision without being influenced by the temperature of the outside space.

Specifically, the influence of the temperature of the outside space can be prevented, since the humidity is obtained with the relational expression in which the temperature of the outside space is not used as a parameter. Moreover, since heat is released forcefully to the outside space from the heat transfer section such that the amount of heat release becomes a predetermined value, the temperature of the heat transfer section is stabilized without being influenced by the temperature of the outside space and fluctuation thereof. Accordingly, the humidity of the measurement space can be obtained with high precision without being influenced by the temperature of the outside space and fluctuation thereof, regardless of the temperature of the heat transfer section that releases heat to the outside space being used as a parameter in the relational expression.

(2) The hygrometer may include a heat transfer section temperature detection unit that detects a temperature of the heat transfer section. In this case, the computation device may use a temperature detected by the heat transfer section temperature detection unit as the temperature of the heat transfer section. The hygrometer may include a measurement space temperature detection unit that detects a temperature of the measurement space. In this case, the computation device may use a temperature detected by the measurement space temperature detection unit as the temperature of the measurement space.

In the case where the hygrometer includes the heat transfer section temperature detection unit and/or the measurement space temperature detection unit as in these configurations, the humidity of the measurement space can be measured without acquiring a heat transfer section temperature and/or a measurement space temperature from an instrument or the like other than the hygrometer.

(3) The hygrometer, specifically, for example, the heat release amount control unit, may include a Peltier element and a power supply unit that supplies power to the Peltier element. In this case, it may be such that the Peltier element is arranged to be capable of cooling the heat transfer section, and the power supply unit is capable of supplying constant power to the Peltier element.

With the configuration, the amount of heat released to the outside space from the heat transfer section can be controlled to be constant. In this case, the Peltier element may be arranged to surround, together with the thermal insulation section, a portion of the heat transfer section other than the portion located within the measurement space. In this case, control of making the amount of heat released to the outside space from the heat transfer section constant can be achieved easily with a simple configuration.

(4) The heat transfer section may protrude toward the outside space side from the thermal insulation section, and the heat release amount control unit may include an air supply section that forms a flow of air toward a portion of the heat transfer section protruding toward the outside space side, and a temperature adjustment section that makes a temperature of air supplied to the protruding portion by the air supply section constant.

With the configuration as well, the amount of heat released to the outside space from the heat transfer section can be controlled to be constant.

(5) The embodiment is a temperature-humidity chamber that has been made by taking note of a relational expression between the respective temperatures and a water vapor pressure of a measurement space, including a thermal insulation section that surrounds a predetermined measurement space, the hygrometer that measures a humidity of the measurement space, and a temperature and humidity adjustment section that adjusts at least one of a humidity and a temperature within the measurement space on the basis of a result of measurement by the hygrometer.

With the configuration, the temperature and the humidity within the measurement space can be adjusted accurately, since the humidity of the measurement space can be obtained with high precision without being influenced by the temperature of the space (outside space) outside the thermal insulation section.

(6) The third embodiment has been made by taking note of a relational expression between the respective temperatures and a water vapor pressure of a measurement space and is a hygrometer that measures a humidity within a space, including a heat transfer section extending from a first end section arranged in a first position within the space up to a second end section arranged in a second position that is apart from the first position, and capable of heat transport of heat that has entered the first end section from the space to the second end section, a heat release amount control unit that causes heat to be released to the space from the second end section of the heat transfer section such that an amount of heat released to the space is made constant, and a computation device that calculates a humidity of the space. The computation device is configured to calculate a humidity of the space from a temperature of the heat transfer section and a temperature of the space using a relational expression based on a heat balance in the heat transfer section when dew formation is occurring at least in the first end section in a state where the amount of heat released to the space from the second end section is made constant by the heat release amount control unit.

With the hygrometer, the humidity of the space at each temperature can be obtained with high precision, even if the temperature of the space fluctuates, by computing the humidity using the relational expression in a state where dew formation has occurred at least in the first end section of the heat transfer section, since heat is released forcefully to the space from the second end section of the heat transfer section such that the released amount of heat (amount of heat release to the space from the heat transfer section) is made constant.

With the embodiment, as described above, the humidity of the measurement space separated from the outside space by the thermal insulation section can be measured with high precision without being influenced by the temperature of the outside space.

The invention claimed is:

1. A temperature-humidity chamber, comprising:
a thermal insulation wall surrounding a predetermined measurement space;
a hygrometer that measures a humidity of the measurement space defined by the thermal insulation wall;
a temperature and humidity adjustment section that adjusts at least one of a humidity and a temperature within the measurement space on a basis of a result of measurement by the hygrometer;
wherein the hygrometer includes:
a heat transfer section having a first end located in the measurement space and a second end opposite to the first end and external of the measurement space;
a heat transfer section temperature sensor provided in the measurement space to detect a temperature of the heat transfer section;
a measurement space temperature sensor provided in the measurement space at a position spaced from the heat transfer section to detect a temperature of the measurement space;
a heat release amount control unit having a power supply unit that outputs a regulated electricity, a contact portion contacting the second end of the heat transfer section and a release portion exposed to the outside space for releasing heat from the heat transfer section to the outside space, the heat release amount control unit being controllable to release a prescribed amount of heat from the release portion to the outside space when powered by the power supply unit;
a computation device that calculates a humidity of the measurement space,
wherein the computation device stores (i) a first formula expressing a relation between a temperature of the heat transfer section, a temperature of the measurement space, an amount of heat released to the outside space from the release portion and a water vapor pressure of the measurement space, (ii) a second formula for calculating a humidity of the measurement space from a water vapor pressure of the measurement space and a saturated water vapor pressure at the temperature of the measurement space, and (iii) data in which a temperature and a saturated water vapor pressure at each temperature are associated, the first formula being based on a base formula associating a sum of sensible heat and latent heat with the amount of heat released to the outside space from the release portion, the sensible heat being a heat that enters the heat transfer section from the measurement space, the latent heat being a heat supplied to the heat transfer section by dew formation on the heat transfer section, the base formula expressing the sum that equals the amount of heat released to the outside space from the release portion, and the computation device includes a first calculating section and a second calculating section, the first calculating section being configured to calculate a water vapor pressure of the measurement space, using the first formula, from a temperature of the heat transfer section detected by the heat transfer section temperature sensor, a temperature of the measurement space detected by the measurement space temperature sensor and the prescribed amount of heat released to the outside space from the release portion when dew formation is occurring in the first end of the heat transfer section located within the measurement space in a state where the amount of heat released to the outside space from the release portion is controlled to the prescribed amount when the heat release amount control unit is powered by the power supply unit, and the second calculating section being configured to calculate a humidity of the measurement space, using the second formula, from the water vapor pressure of the measurement space calculated using the first formula and the saturated water vapor pressure at the temperature of the measurement space obtained using the data.

2. The temperature-humidity chamber according to claim 1, wherein the heat release amount control unit includes a Peltier element that is arranged to be capable of cooling the heat transfer section, and
the power supply unit is capable of supplying constant power to the Peltier element.

3. The temperature-humidity chamber according to claim 2, wherein the Peltier element is arranged to surround, together with the thermal insulation wall, a portion of the heat transfer section other than the portion located within the measurement space.

4. The temperature-humidity chamber according to claim 1, wherein the heat transfer section protrudes toward the outside space side from the thermal insulation wall, and
the heat release amount control unit includes an air supply section that forms a flow of air toward a portion of the heat transfer section protruding toward the outside space side, and a temperature adjustment section that makes a temperature of air supplied to the portion of the heat transfer section by the air supply section constant.

5. A temperature-humidity chamber, comprising:
a thermal insulation section that defines a predetermined space;
a hygrometer that measures a humidity within the space;
a temperature and humidity adjustment section that adjusts at least one of a humidity and a temperature within the space on a basis of a result of measurement by the hygrometer, wherein the hygrometer includes:
a heat transfer section having a first end section and a second end section, the heat transfer section extending from the first end section arranged in a first position within the space up to a second end section arranged in a second position that is apart from the first position within the space, and capable of heat transport of heat that has entered the first end section from the space to the second end section;
a heat transfer section temperature sensor provided in the space to detect a temperature of the heat transfer section;

a space temperature sensor provided in the space to detect a temperature of the space at a position spaced from the heat transfer section;

a heat release amount control unit having a power supply unit that outputs a regulated electricity, a contact portion contacting with the second end section of the heat transfer section and a release portion exposed to the space for releasing heat from the heat transfer section to the space, the heat release amount control unit that can be controlled to release a prescribed amount of heat to the space from the release portion when powered by the power supply unit; and a computation device that calculates a humidity of the space, wherein the computation device stores (i) a first formula expressing a relation between a temperature of the heat transfer section, a temperature of the space, an amount of heat released to the space from the release portion and a water vapor pressure of the space, (ii) a second formula for calculating a humidity of the space from a water vapor pressure of the space and a saturated water vapor pressure at the temperature of the space, and (iii) data in which a temperature and a saturated water vapor pressure at each temperature are associated, the first formula being based on a base formula associating a sum of sensible heat and latent heat with the amount of heat released to the space from the release portion, the sensible heat being a heat that enters the heat transfer section from the space, the latent heat being a heat supplied to the heat transfer section by dew formation on the heat transfer section, the base formula expressing the sum that equals the amount of heat released to the space from the release portion, and the computation device includes a first calculating section and a second calculating section, the first calculating section being configured to calculate a water vapor pressure of the space, using the first formula, from a temperature of the heat transfer section detected by the heat transfer section temperature sensor, a temperature of the space detected by the space temperature sensor and the prescribed amount of heat released to the space from the release portion when dew formation is occurring at least in the first end section in a state where the amount of heat released to the space from the release portion is controlled to the prescribed amount when the heat release amount control unit is powered by the power supply unit, and the second calculating section being configured to calculate a humidity of the space, using the second formula, from the water vapor pressure of the space calculated using the first formula and the saturated water vapor pressure at the temperature of the space obtained using the data.

* * * * *